United States Patent
Reyes et al.

(10) Patent No.: US 11,707,617 B2
(45) Date of Patent: Jul. 25, 2023

(54) METHOD TO EXTRACT AND QUANTIFY THE CARDIAC END DIASTOLIC POINT/MITRAL VALVE CLOSING POINT FROM THE HVAD ESTIMATED FLOW WAVEFORM

(71) Applicant: HeartWare, Inc., Miami Lakes, FL (US)

(72) Inventors: Carlos Reyes, Davie, FL (US); Neethu Lekshmi Vasudevan Jalaja, Miami Lakes, FL (US)

(73) Assignee: HeartWare, Inc., Miami Lakes, FL (US)

( * ) Notice: Subject to any disclaimer, the term of this patent is extended or adjusted under 35 U.S.C. 154(b) by 332 days.

(21) Appl. No.: 17/095,096

(22) Filed: Nov. 11, 2020

(65) Prior Publication Data
US 2021/0154384 A1    May 27, 2021

Related U.S. Application Data

(60) Provisional application No. 62/939,158, filed on Nov. 22, 2019.

(51) Int. Cl.
| A61M 60/216 | (2021.01) |
| A61M 60/546 | (2021.01) |
| A61M 60/538 | (2021.01) |
| A61M 60/148 | (2021.01) |
| A61M 60/422 | (2021.01) |

(52) U.S. Cl.
CPC ........ *A61M 60/538* (2021.01); *A61M 60/148* (2021.01); *A61M 60/422* (2021.01); *A61M 2205/18* (2013.01); *A61M 2205/3331* (2013.01); *A61M 2230/04* (2013.01)

(58) Field of Classification Search
CPC ...... A61M 2205/18; A61M 2205/3331; A61M 2230/04; A61M 60/148; A61M 60/178; A61M 60/216; A61M 60/232; A61M 60/422; A61M 60/538; A61M 60/546
See application file for complete search history.

(56) References Cited

U.S. PATENT DOCUMENTS

| 6,688,861 | B2 | 2/2004 | Wampler |
| 7,575,423 | B2 | 8/2009 | Wampler |
| 7,976,271 | B2 | 7/2011 | LaRose et al. |
| 8,135,468 | B2 | 3/2012 | Gutfinger et al. |
| 8,209,001 | B2 | 6/2012 | Shelchuk et al. |
| 8,419,609 | B2 | 4/2013 | Shambaugh, Jr. et al. |
| 9,039,595 | B2 | 5/2015 | Ayre et al. |
| 2008/0097226 | A1 | 4/2008 | McConnel |
| 2014/0142444 | A1 | 5/2014 | Ngo et al. |

(Continued)

OTHER PUBLICATIONS

International Search Report and Written Opinion dated Mar. 26, 2021, for corresponding International Application No. PCT/US2020/060661; International Filing Date: Nov. 16, 2020 consisting of 8-pages.

*Primary Examiner* — Jon Eric C Morales
(74) *Attorney, Agent, or Firm* — Shumaker & Sieffert, P.A.

(57) ABSTRACT

A control circuit for a sensorless implantable blood pump configured to determine mitral valve regurgitation includes processing circuitry configured to generate an estimated blood flow waveform from the sensorless implanted blood pump and generate an alert if between an end period of diastole and a beginning period of systole a measured amplitude of the estimated blood flow waveform does not include an inflection point.

18 Claims, 5 Drawing Sheets

(56) References Cited

U.S. PATENT DOCUMENTS

| | | |
|---|---|---|
| 2015/0174307 A1 | 6/2015 | Eckman et al. |
| 2015/0367048 A1 | 12/2015 | Brown et al. |
| 2018/0028735 A1 | 2/2018 | Demou et al. |
| 2018/0214696 A1 | 8/2018 | Cuchiara et al. |

METHOD TO EXTRACT AND QUANTIFY THE CARDIAC END DIASTOLIC POINT/MITRAL VALVE CLOSING POINT FROM THE HVAD ESTIMATED FLOW WAVEFORM

CROSS-REFERENCE TO RELATED APPLICATION

This application claims the benefit of U.S. Application Ser. No. 62/939,158, filed Nov. 22, 2019.

FIELD

The present application is generally related to a system for determining mitral valve function and cardiac preload in a patient having an implantable blood pump.

BACKGROUND

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as a ventricular assist device or "VAD." Where a VAD is used to assist the pumping action of the left ventricle, the device draws blood from the left ventricle of the heart and discharges the blood into the aorta.

In cardiac physiology preload is defined as the initial stretching of the cardiac myocytes prior to contraction. The sarcomere length cannot be determined directly, other indices of preload such as left atrial pressure (LAP), left ventricular end diastolic pressure, and ventricular end diastolic volume (EDV) are used to define the preload. In a failing heart, preload will not necessarily increase the stroke volume as the ventricle cannot be stretched more which can lead to systemic congestion or edema. In mechanical circulatory support (MCS) therapy, the VAD is placed in the left and/or right ventricle to assist the failing ventricle to migrate the available/residual volume of blood from ventricle into the systemic/pulmonary circulation for appropriate perfusion. Operating the pump at a predetermined set speed maintains the physiologically suitable output and prevent ventricle overfilling/suction which arises due to under/over pumping. However, current VAD devices do not have an efficient preload tracking method to derive the preload information or are configured to determine mitral valve regurgitation without using sensors directly.

SUMMARY

The techniques of this disclosure generally relate to utilizing the trough to peak rise phase of HVAD estimated flow waveform to predict the mitral valve status. Under normal physiologic condition, the mitral valve closing point, noted by a notch in the waveform changes based on the ventricular pressure. At higher pulmonary capillary wedge pressure (PCWP), mitral valve must work against more pressure causing the shift in the point. Hence the distance of this notch from waveform trough can be used as a surrogate for ventricular volume or preload. The proposed method offers a non-invasive way to extract preload information from HVAD current waveform which reflects preload changes in its morphology.

In one aspect, a control circuit for a sensorless implantable blood pump configured to determine mitral valve regurgitation includes processing circuitry configured to generate an estimated blood flow waveform from the sensorless implanted blood pump and generate an alert if between an end period of diastole and a beginning period of systole a measured amplitude of the estimated blood flow waveform does not include an inflection point.

In another aspect of this embodiment, the estimated blood flow waveform is based on current supplied to the sensorless implanted blood pump.

In another aspect of this embodiment, the sensorless implanted blood pump is a ventricular assist device.

In another aspect of this embodiment, the sensorless implanted blood pump is a centrifugal pump.

In another aspect of this embodiment, the sensorless implanted blood pump is electrically coupled to at least one from the group consisting of an implanted controller and an external controller.

In another aspect of this embodiment, the control circuit is further configured to periodically measure the amplitude of the estimated blood flow between an end period of diastole and a beginning period of systole.

In another aspect of this embodiment, an absence of the inflection point is indicative of mitral valve regurgitation.

In another aspect of this embodiment, the generated alert includes a prompt to adjust the speed of the sensorless implanted blood pump.

In another embodiment, a control circuit for a sensorless implantable blood pump includes processing circuitry configured to generate at least one from the group consisting of an estimated current waveform and flow waveform from the sensorless implanted blood pump; determine a mitral valve closing point from the estimated at least one form the group consisting of current waveform and flow waveform from the sensorless implanted blood pump; calculate a preload relative indicator; compare the preload relative indicator with a normal baseline preload relative indicator; and adjust the speed of the pump based on the comparison.

In another aspect of this embodiment, the processing circuitry is configured to calculate the preload relative indicator by dividing a measured amplitude between the mitral valve closing point and a trough of the estimated at least one form the group consisting of current waveform and flow waveform by a measured amplitude between a peak of the at least one form the group consisting of current waveform and flow waveform and the trough.

In another aspect of this embodiment, the sensorless implanted blood pump is a ventricular assist device.

In another aspect of this embodiment, the sensorless implanted blood pump is a centrifugal pump.

In another aspect of this embodiment, the processing circuitry is configured to generate an alert if the preload index deviates from the normal baseline preload relative indicator by a predetermined percentage.

In another aspect of this embodiment, the processing circuitry is configured to increase the speed of the pump if the preload relative indicator is greater than the normal baseline preload relative indicator by a predetermined percentage.

In another aspect of this embodiment, the predetermined percentage is between 5-15%.

In another aspect of this embodiment, the processing circuitry is configured to decrease the speed of the pump if the preload relative indicator is less than the normal baseline preload by a predetermined percentage.

In another aspect of this embodiment, the predetermined percentage is between 5-15%.

In another embodiment, a control circuit for a sensorless implantable blood pump includes processing circuitry is configured to: generate at least one from the group consisting of an estimated current waveform and flow waveform from the sensorless implanted blood pump; determine a mitral valve closing point from the estimated at least one form the group consisting of current waveform and flow waveform from the sensorless implanted blood pump; calculate a preload relative indicator by dividing a measured amplitude between the mitral valve closing point and a trough of the estimated at least one form the group consisting of current waveform and flow waveform by a measured amplitude between a peak of the at least one form the group consisting of current waveform and flow waveform and the trough; compare the preload relative indicator with a normal baseline preload; and generate an alert if the preload relative indicator deviates from the normal baseline preload by a between 5-15%.

The details of one or more aspects of the disclosure are set forth in the accompanying drawings and the description below. Other features, objects, and advantages of the techniques described in this disclosure will be apparent from the description and drawings, and from the claims

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
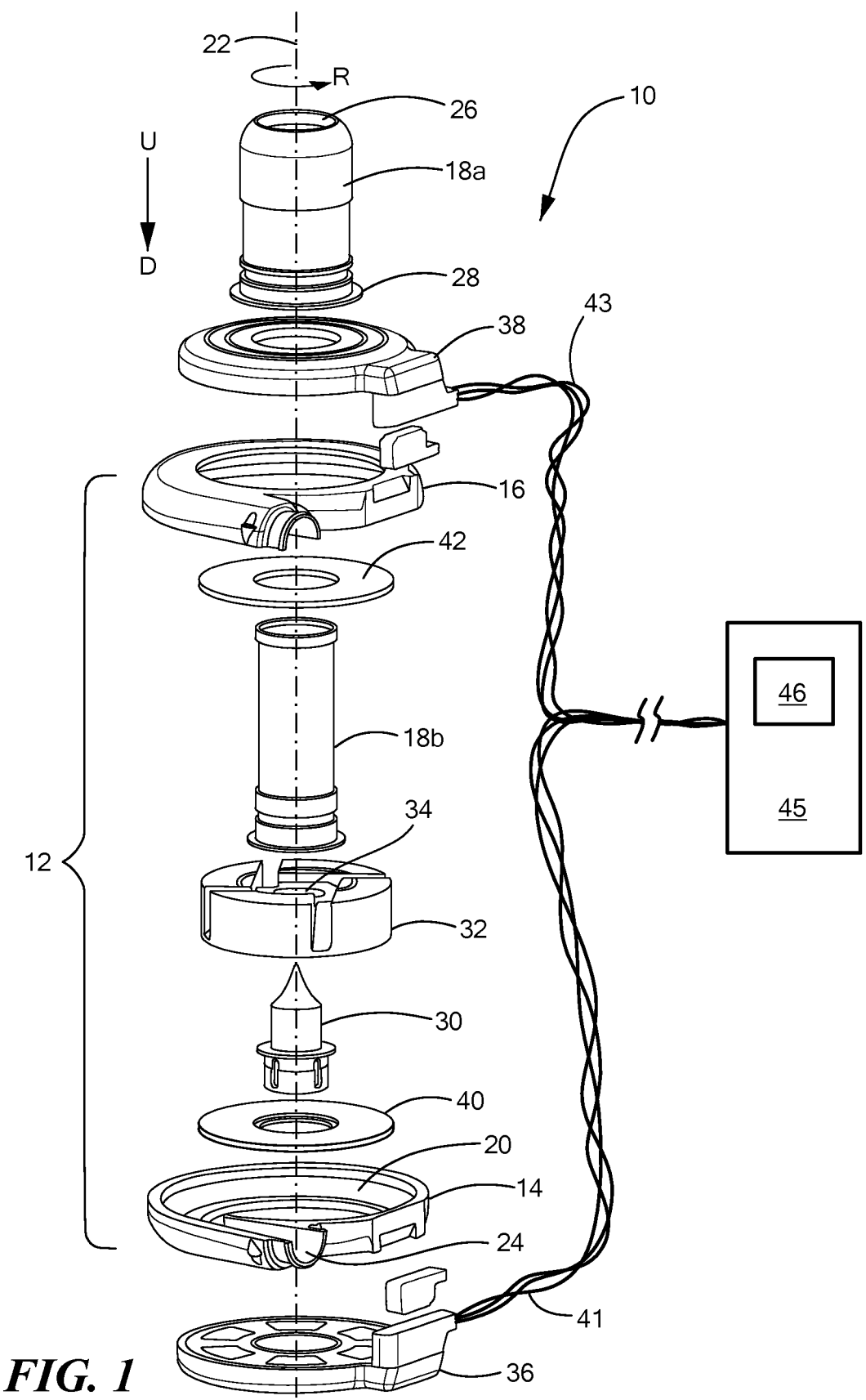
FIG. 1 is a disassembled view of an implantable blood pump constructed in accordance with the principles of the present application.

Referring now to the drawings in which like reference designators refer to like elements there is shown in FIG. 1 an exemplary sensorless blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

The inflow cannula 18 is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated in FIG. 1 by the arrows U and D respectively. A post 30 is mounted to first portion 14 along axis 22. A generally disc shaped ferromagnetic rotor 32 with a central hole 34 is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

Electrical connectors 41 and 43 are provided on the first stator 36 and the second stator 38 respectively for connecting the coils to a source of power such as a controller 45, which may be implanted or external to the patient. The controller 45 is arranged to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with elements of the first portion 14 and the second portion 16 during operation, as discussed in more detail below. The general arrangement of the components described above may be similar to the blood pump 10 used in the MCSD sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein.

Figure 2:
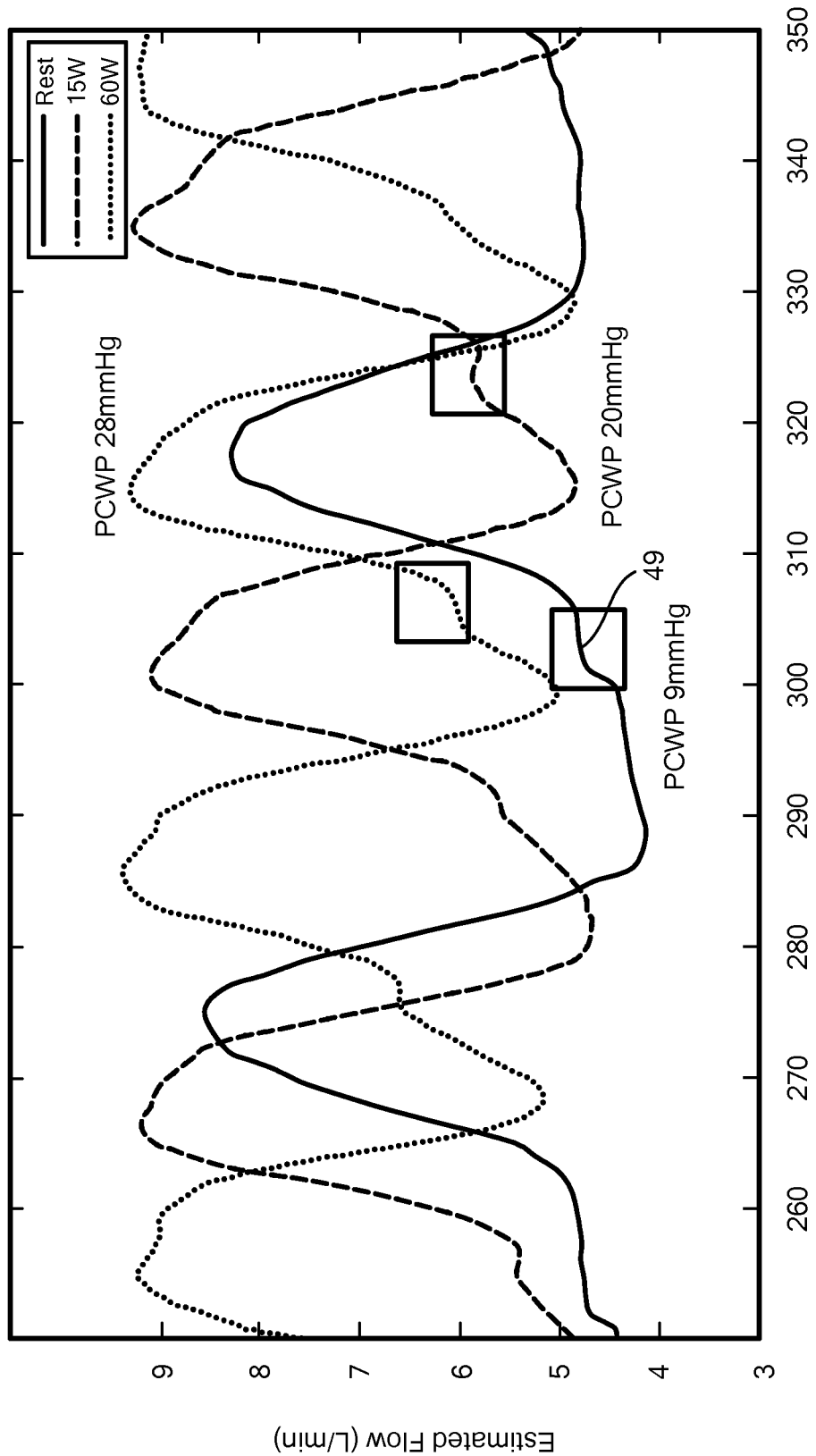
FIG. 2 is a graph showing the estimated flow waveform at various exercise conditions and the location of the mitral valve closing point shifts as exercise increases.

Referring now to FIG. 2, in one configuration, the controller 45 is configured to provide 50 Hz high-resolution data of pump 10 parameters, for example, speed, current, and voltage, as well as a flow estimation calculation. In one configuration, the controller 45 maintains a constant pump set speed of the impeller 32, as selected by the user. The pump set speed is set as to provide adequate positive flow through the pump, i.e. the pump 10 generates sufficient pressure to overcome systemic pressure for positive flow. Increase in pump preload, i.e. more volume in ventricle or a decrease in systemic resistance can aid in positive flow, as in both instances, differential pressure across the pump is decreased. During a normal cardiac cycle, pump flow will increase with decrease in differential pressure (i.e. systole) and will decrease with an increase in differential pressure across the pump (i.e. diastole). Additionally, the operation of aortic and mitral valve may cause changes in flow patterns that may be reflected in the morphology of estimated flow waveform which can be used as markers to identify the status of valve operation. For example, as shown in FIG. 2, under normal physiologic condition, the mitral valve closing point, noted by the change in slope of the estimated flow, which appears as a notch in the boxes in FIG. 2, based on the ventricular pressure. At higher pulmonary capillary wedge pressure (PCWP), the mitral valve must work against more pressure causing the shift in the point at which the mitral valve closes. Hence, the distance of this change in slope from the estimated flow waveform trough may be used as a surrogate for ventricular volume or preload, as discussed in more detail below.

Figure 3:
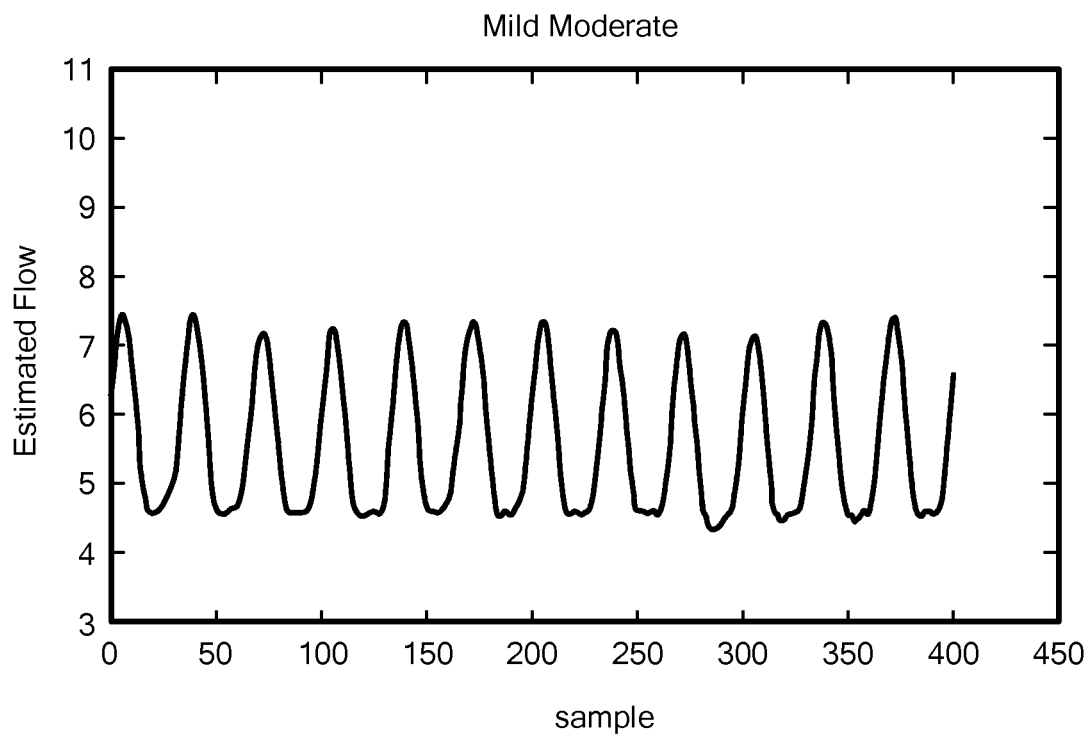
FIG. 3 is a graph showing the estimated flow waveform in a patient with moderate mitral valve regurgitation.
Figure 4:
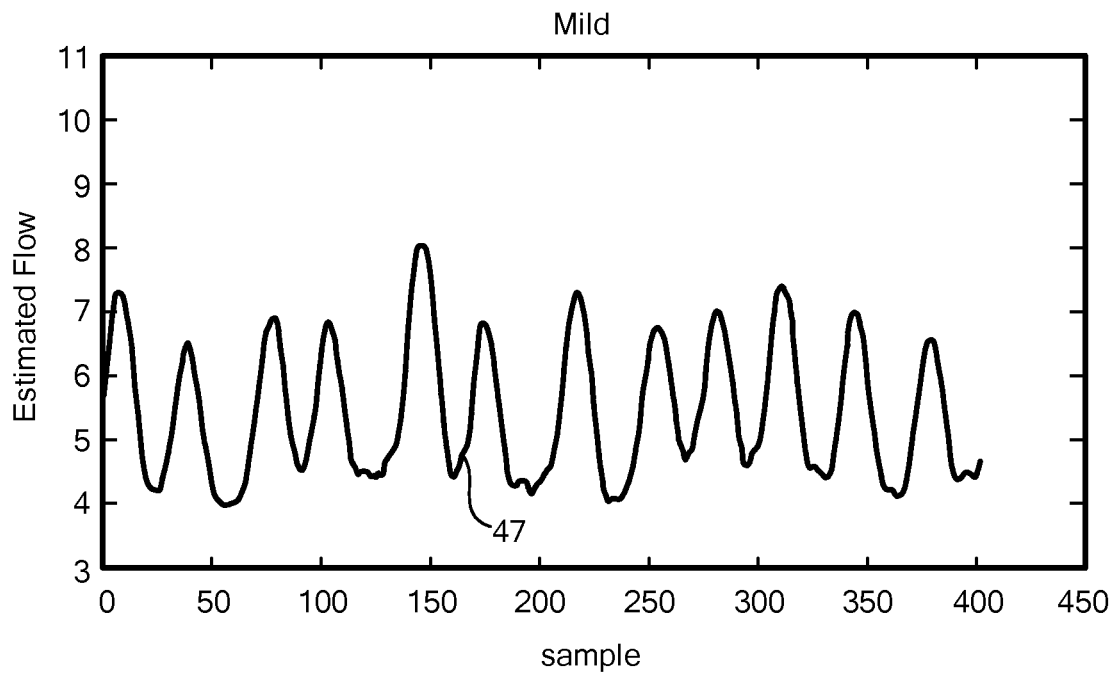
FIG. 4 is a graph showing the estimated flow waveform in a patient with mild mitral valve regurgitation.

Referring now to FIGS. 3-4, abnormalities such as mitral valve regurgitation associated with mitral valve malfunction maybe reflected in the estimated flow waveform as well. Based on the severity of regurgitation, waveform morphology changes. The severity of mitral regurgitation (MR) is grouped as control/trivial (no MR), mild, mild-moderate based on the available clinical data. As the severity increases, the mitral valve closing point disappears as the valve is not closing completely and trough appears flat and does not include an inflection point or notch. In another words, the amplitude of the estimated flow waveform includes inflection point between the end of diastole and the beginning of systole when the mitral valve is functioning normally. When the mitral valve is not functioning normally, the inflection point disappears.

In one configuration, the controller 45 has a control circuit 46 having processing circuitry configured to compare a first amplitude 47 of the estimated flow waveform at, for example, a predetermined interval during an end period of diastole with a second amplitude 49 of a predetermined normal baseline estimated flow waveform during the same time period (FIG. 2). For example, the normal baseline estimated flow waveform may be from the patient or a generic known baseline from a patient not exhibiting MR. Such a baseline includes an inflection point in the amplitude between the end period of diastole and the beginning of systole. The control circuit 46 is further configured to determine if the first amplitude 47 includes an inflection point by, for example, a point in which the amplitude turns negative or otherwise flattens between the end period of diastole and a beginning period systole. If there is no point between the end period of diastole and a beginning period systole where the first amplitude 47 changes slop or turns negative, an alert may be generated by the control circuit 46 indicating MR. The assessment of the first amplitude 47 compared may be made during a single time period, during a single cardiac cycle, or at intervals over multiple cardiac cycles. As the severity of MR increases, the amplitude between the end of diastole and the beginning of systole becomes flat, as shown in FIG. 3-4.

Figure 5:
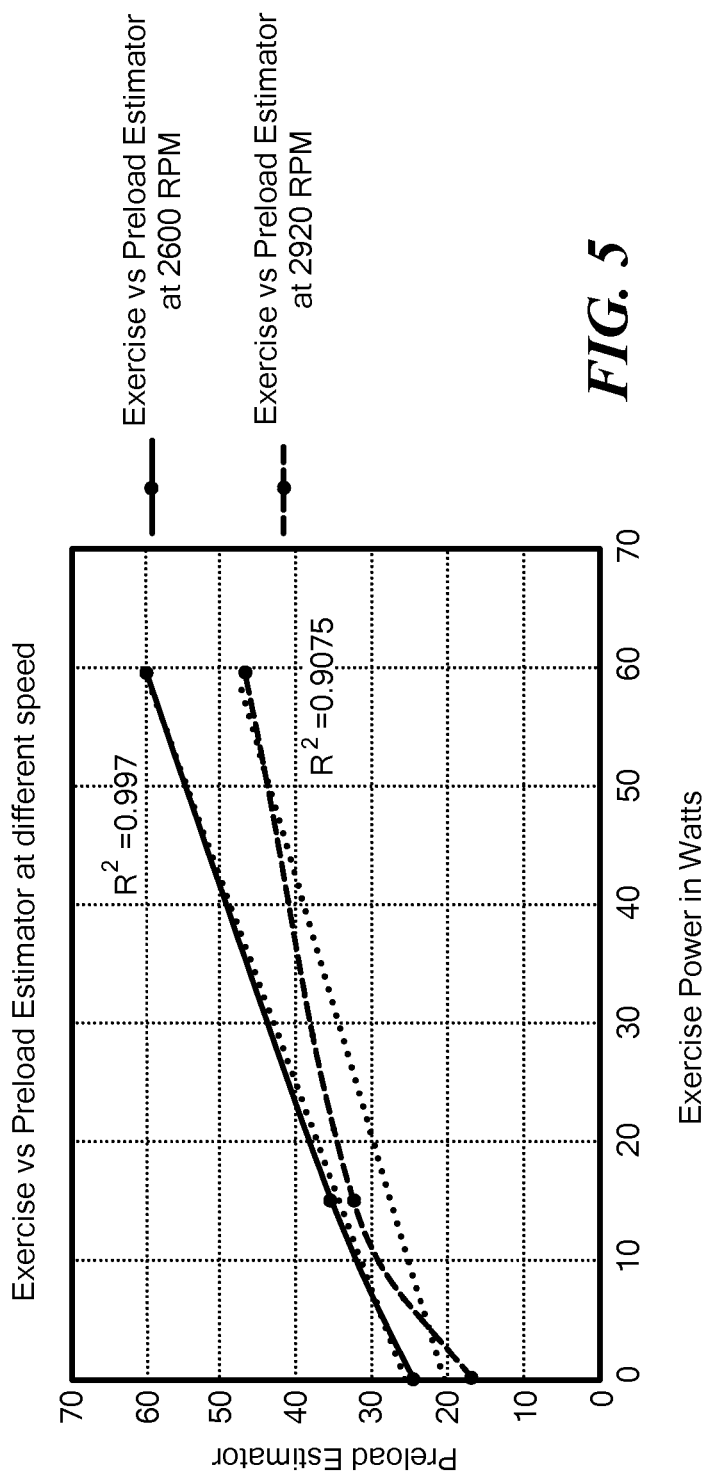
FIG. 5 is a graph showing that the estimated preload returns to normal after a pump speed is increased.

Referring now to FIG. 5, left ventricle pressure (LVP), which is one factor that drives pump 10 flow and the ventricular end diastolic pressure point creates a change in the slope in the estimated flow waveform, which corresponds to the mitral valve closing point as discussed above. For a given preload, the pressured required to close the mitral valve depends on LVP. As preload increases, the mitral valve works against the increase in pressures to close the mitral valve and the mitral valve closing points shifts up in the waveform. The percentage or magnitude increase of the shift in the mitral valve closing point with respect to changes in LVP may be monitored to provide ventricular preload information. For example, as a person exercises the preload increases to accommodate the increase need for blood flow. As shown in FIG. 5, which is a graph showing the effect of impeller 32 speed on preload. A patient initially operating at baseline impeller 32 speed (2600 RPM) performing exercise at 0W, 15 W, and 60 W. The preload increases for the given speed. When the speed is increased to 2920 RPM and the same exercises are performed again. The preload level decreases compared to the preload at the lower speed of 2600 RPM.

Figure 6:
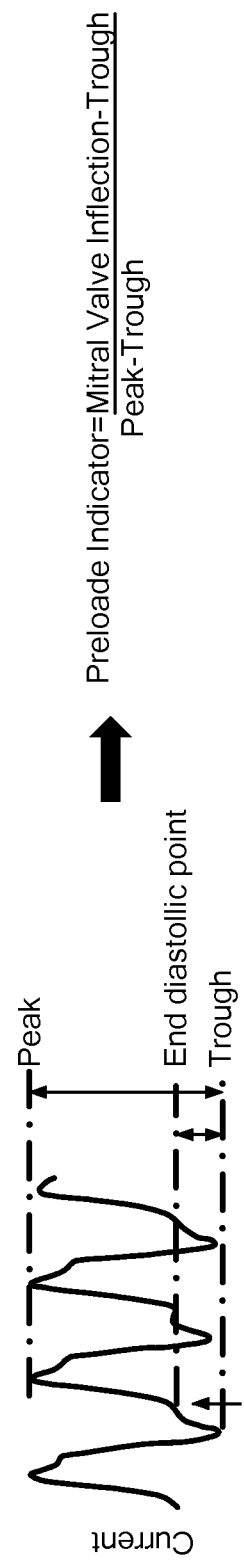
FIG. 6 is a graph. showing the calculation of the preload relative indicator.
Figure 7:
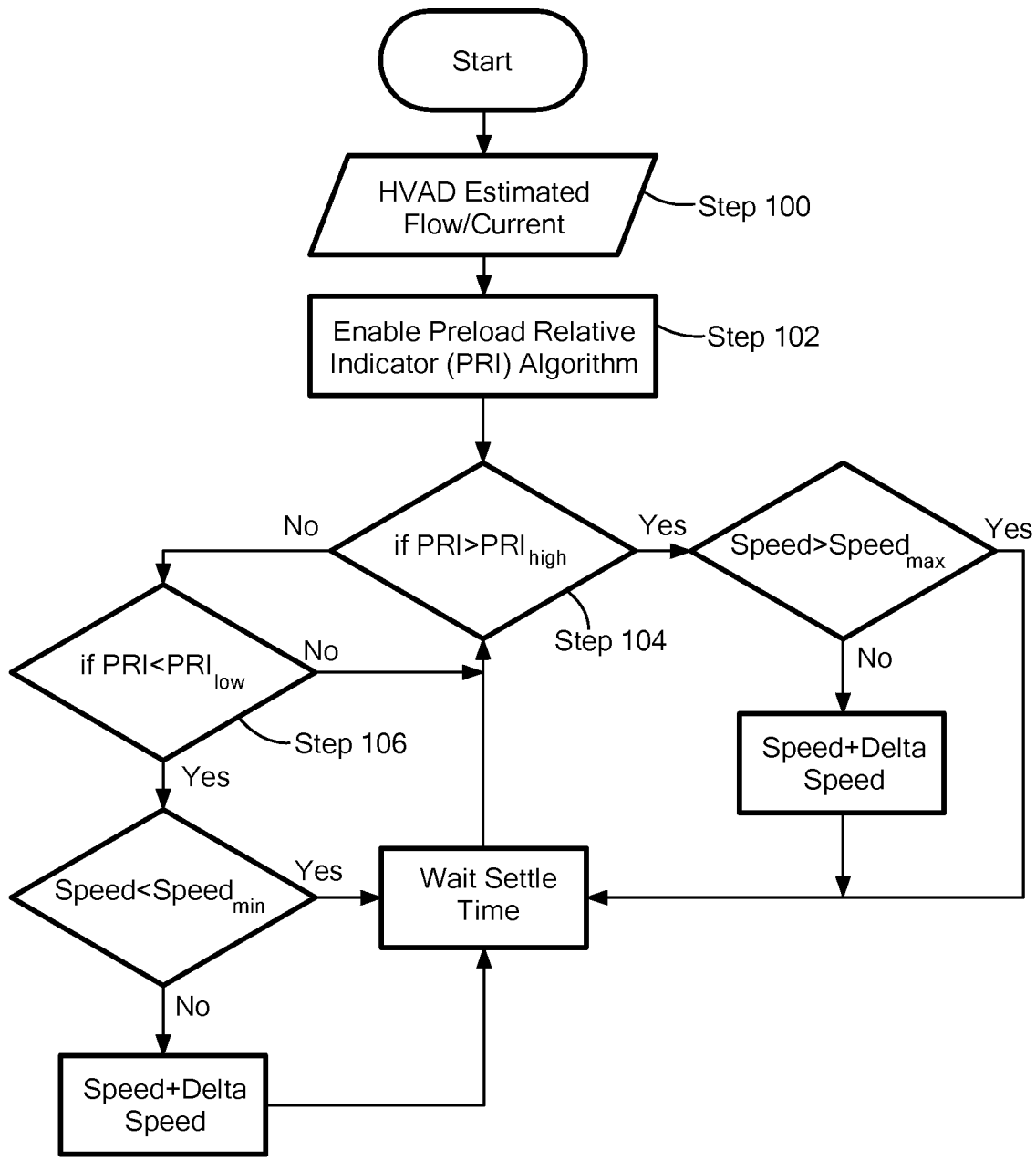
FIG. 7 is a flow chart showing the steps of determining cardiac preload in a patient having an implantable blood pump.

Referring now to FIGS. 6-7, the control circuit 46 may be configured to generate an estimated current or flow waveform from the sensorless implanted blood pump 10 (Step 100). The estimated current or flow waveform may be derived from the measured current information from the pump 10 in a patent that does not have MR. The control circuit 46 may then extract the patient's systolic-diastolic cycle based on the estimated current or flow waveform and determine the mitral valve closing point. The mitral valve closing point may then be determined and the magnitude of the flow or current waveform for the estimated flow waveform are measured at the mitral valve closing point. The control circuit 46 may then calculate a patient preload relative indicator (PRI) (Step 102), which is a relative indicator of the particular patient's preload, calculated by the following formula, as shown in FIG. 6:

$$\text{Preload Relative Indicator } (PRI) = \frac{\text{Mitral Valve Infection} - \text{Trough}}{\text{Peak} - \text{Trough}}$$

That is, the PRI is equal to the amplitude of the current or flow between the mitral valve closing point and the trough divided by the peak to trough current or flow. As preload increases, left atrial pressure increase and the end diastolic point shift upwards and vice versa. The percentage or magnitude increase, or decrease, in the calculated PRI is compared to a normal baseline preload relative indicator range to determine if a speed of the impeller 32 should be changed based on the calculated PRI. In particular, if the calculated PRI is greater than a normal baseline PRI range Step (104), for example, by 5-15%, meaning there is excess volume in the ventricle and thus excess pressure, then the control circuit 46 may increase the speed of the impeller 32. If the pump 10 is already operating at a maximum speed, then the PRI is remeasured after a predetermined period of time and compared against the normal baseline PRI range before a speed change is made. If the PRI is less than the normal baseline range (Step 106), for example, by 5-15%, then the speed of the impeller 32 may be decreased. If the pump 10 is already operating at a minimum speed, then the PRI is remeasured after a predetermined period of time and compared against the normal baseline PRI range before a speed change is made.

Referring back now to FIG. 5, the above method may be utilized to return the patient's preload index to a normal baseline preload. For example, the $R^2$ value for increase in preload owing to exercise in watts a patient versus the above method's preload index predictor shows a high correlation when measured at, for example, 2600 RPM or 2920 RPM. In particular, at 2920 RPM, when the impeller 32 speed is increased, the preload index returns to the normal baseline pressure It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A control circuit for a sensorless implantable blood pump configured to determine mitral valve regurgitation, the control circuit comprising:
processing circuitry configured to:
generate an estimated blood flow waveform from the sensorless implanted blood pump; and
generate an alert if between an end period of diastole and a beginning period of systole a measured amplitude of the estimated blood flow waveform does not include an inflection point.

2. The control circuit of claim 1, wherein the estimated blood flow waveform is based on current supplied to the sensorless implanted blood pump.

3. The control circuit of claim 1, wherein the sensorless implanted blood pump is a ventricular assist device.

4. The control circuit of claim 1, wherein the sensorless implanted blood pump is a centrifugal pump.

5. The control circuit of claim 1, wherein the sensorless implanted blood pump is electrically coupled to at least one from the group consisting of an implanted controller and an external controller.

6. The control circuit of claim 1, wherein the control circuit is further configured to periodically measure the amplitude of the estimated blood flow between an end period of diastole and a beginning period of systole.

7. The control circuit of claim 1, wherein an absence of the inflection point is indicative of mitral valve regurgitation.

8. The control circuit of claim 1, wherein the generated alert includes a prompt to adjust the speed of the sensorless implanted blood pump.

9. A control circuit for a sensorless implantable blood pump, the control circuit comprising:
processing circuitry configured to:
generate at least one from the group consisting of an estimated current waveform and flow waveform from the sensorless implanted blood pump;
determine a mitral valve closing point from the estimated at least one from the group consisting of current waveform and flow waveform from the sensorless implanted blood pump;
calculate a preload relative indicator;
compare the preload relative indicator with a normal baseline preload relative indicator; and
adjust the speed of the pump based on the comparison.

10. The control circuit of claim 9, wherein the processing circuitry is configured to calculate the preload relative indicator by dividing a measured amplitude between the mitral valve closing point and a trough of the estimated at least one from the group consisting of current waveform and flow waveform by a measured amplitude between a peak of the at least one from the group consisting of current waveform and flow waveform and the trough.

11. The control circuit of claim 9, wherein the sensorless implanted blood pump is a ventricular assist device.

12. The control circuit of claim 9, wherein the sensorless implanted blood pump is a centrifugal pump.

13. The control circuit of claim 9, wherein the processing circuitry is configured to generate an alert if the preload relative indicator deviates from the normal baseline preload relative indicator by a predetermined percentage.

14. The control circuit of claim 9, wherein the processing circuitry is configured to increase the speed of the pump if the preload relative indicator is greater than the normal baseline preload relative indicator by a predetermined percentage.

15. The control circuit of claim 14, wherein the predetermined percentage is between 5-15%.

16. The control circuit of claim 9, wherein the processing circuitry is configured to decrease the speed of the pump if the preload relative indicator is less than the normal baseline preload by a predetermined percentage.

17. The control circuit of claim 16, wherein the predetermined percentage is between 5-15%.

18. A control circuit for a sensorless implantable blood pump, the control circuit comprising:
processing circuitry configured to:
generate at least one from the group consisting of an estimated current waveform and flow waveform from the sensorless implanted blood pump;
determine a mitral valve closing point from the estimated at least one from the group consisting of current waveform and flow waveform from the sensorless implanted blood pump;
calculate a preload relative indicator by dividing a measured amplitude between the mitral valve closing point and a trough of the estimated at least one from the group consisting of current waveform and flow waveform by a measured amplitude between a peak of the at least one from the group consisting of current waveform and flow waveform and the trough;
compare the preload relative indicator with a normal baseline preload; and generate an alert if the preload relative indicator deviates from the normal baseline preload by a between 5-15%.

* * * * *